United States Patent [19]

Felauer et al.

[11] 4,054,585

[45] Oct. 18, 1977

[54] FURAN-3-CARBOXAMIDE DERIVATIVES AND METHOD OF PREPARING SAME

[75] Inventors: Ethel E. Felauer; Marshall Kulka, both of Guelph, Canada; Bogislav Von Schmeling, Hamden; Robert A. Davis, Cheshire, both of Conn.

[73] Assignee: Uniroyal, Inc., Naugatuck, Conn.

[21] Appl. No.: 694,479

[22] Filed: June 9, 1976

Related U.S. Application Data

[63] Continuation of Ser. No. 232,293, March 6, 1972, abandoned, which is a continuation of Ser. No. 799,109, Feb. 13, 1969, abandoned.

[51] Int. Cl.$^2$ .......................................... C07D 307/68
[52] U.S. Cl. .......................... 260/347.3; 260/295 AM; 260/294.8 R; 260/302 H; 260/346.73; 260/347.2; 260/346.22; 544/152
[58] Field of Search .................. 260/347.3, 247.7 A, 260/295, 302 H, 346.2 R, 347.2

[56] References Cited

U.S. PATENT DOCUMENTS 3,352,663  11/1967  Freund et al. ............... 260/347.3

OTHER PUBLICATIONS

Hanson et al. J. Am. Chem. Soc. (1965) pp. 5984–5988.
Reichstein et al., Helv. Chim. Acta (1932) vol. 15, pp. 1105–1107.
Gonsalez, Advances in Carbohydrate Chem. (1956) vol. 11, pp. 97–109.
Paul et al., Bull. de la Societe Chimique de France (1968) No. 5, pp. 2134–2138.

Primary Examiner—Henry R. Jiles
Assistant Examiner—Bernard Dentz
Attorney, Agent, or Firm—Hubbell, Cohen, Stiefel & Gross

[57] ABSTRACT

A broad class of furan-3-Carboxamide derivatives, including many novel compounds, can be made reliably and in good yields by a novel one step reaction between an α-hydroxyketone and an acetamide in the presence of a Friedel-Crafts agent in an inert solvent. The broad class of derivatives has fungicidal and insecticidal utility.

21 Claims, No Drawings

FURAN-3-CARBOXAMIDE DERIVATIVES AND METHOD OF PREPARING SAME

This is a continuation, of application Ser. No. 232,293, filed Mar. 6, 1972 which is now abandoned, which is a continuation of application Ser. No. 799,109, filed Feb. 13, 1969, and which is now abandoned.

This invention relates to a broad class of novel furan-3-carboxamide derivatives which possess good fungicidal and insecticidal properties, and to a novel one step method for their preparation. The furan-3-carboxamide derivatives of the invention can be represented by the following generic structural formula:

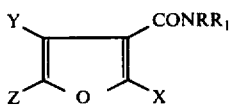

where X, Y, and Z can be independently selected from H, $NH_2$-, methyl, other alkyl, substituted alkyl (e.g., hydroxyalkyl, chloroalkyl, nitroalkyl), halo, alkenyl, Y and Z together are a W-alkylene, phenyl, substituted phenyl (e.g. alkylphenyl, halophenyl, alkoxyphenyl), R is selected from H, methyl, other alkyl, acyl, aroyl, sulfenyl; $R_1$ is selected from phenyl, substituted phenyl (e.g., alkylphenyl, alkoxyphenyl, halophenyl, nitrophenyl), benzyl, bi-phenylyl, alkyl, alkenyl, cycloalkyl, naphthyl, pyridyl, thiazolyl, furfuryl, ethylene bis-; and $RR_1$ can be a ring structure such as morpholido.

There are surprisingly few known furan-3-carboxamide derivatives. These are:

a. 2-methyl furan -3-N, aminocarboxamide (X = $Ch_3$, Y and Z = H, R = H, $R_1$ = $NH_2$ b. 2-methyl furan-3-carboxanilide (X = $CH_3$, Y and Z = H, R = H, $R_1$ = phenyl)

c. 2,4-dimethyl furan-3-carboxanilide (X and Y = $Ch_3$, Z = H, R = H, $R_1$ = phenyl)

d. 2,4,5-trimethyl furan-3-carboxamide (X, Y and Z = $CH_3$, R = $R_1$ = H)

None of these known compounds, however, has ever been described as a fungicidal or insecticidal chemical. Their usefulness as such is disclosed in detail in the copending application of Davis et al., Ser. No. 799,110 filed of even date herewith and assigned to the same assignee as is the instant application and now U.S. Pat. No. 3,959,481.

It is a significant and important aspect of the invention that furan-3-carboxamide derivatives, whether new or those few previously known, can be prepared in accordance with a novel one step method that promises to be of important commercial significance. The method comprises reacting an α -hydroxyketone (I) with an acetamide (II), in an inert solvent (such as benzene, toluene or xylene or mixtures thereof), with an active Friedel-Crafts reagent (such as $AlCl_3$, $AlBr_3$ or $SnCl_4$), to produce the carboxamide derivative (III).

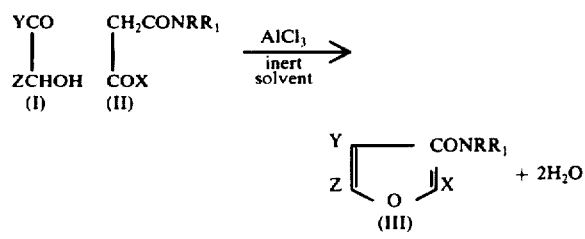

$AlCl_3$, $AlBr_3$ and $SnCl_4$ are preferred Friedel-Crafts reagents ($ZnCl_2$ and $BF_3$, for example, tend to produce pyrrole structures). It has been found convenient to use about 0.5 mole of the selected Friedel-Crafts reagent for each mole of α-hydroxyketone or acetamide used, and to use equimolar quantities of the latter reagents.

As the ring closure is accompanied by the expulsion of water, a strongly dehydrating Friedel-Crafts reagent is preferred. On the other hand, it is possible to use just a catalytic amount of the Friedel-Craft reagent (i.e. 0.01 to 0.50 mole per mole α-hydroxyketone or acetamide) and to remove the water of reaction by some other means as, for example, by removing it azeotropically in a Dean-Stark trap, or by including an inert dehydrating agent.

Since Friedel-Crafts reagents will react with hydroxy groups, it is preferable to employ anhydrous reactants and nonhydroxylic solvents such as, for example, in addition to those mentioned above, nitrobenzene, chlorobenzene, ethyl acetate and acetonitrile.

As noted, it is convenient to use equimolar amounts of the α-hydroxyketone and acetamide reactants. The reaction is exothermic, although some heating at the start of the reaction is preferred; heating to temperatures of about 50° C. or higher suffices. Preferably neither the initial temperature nor the temperature resulting from the heat of reaction should exceed the boiling point of the reacting solution.

After completion of the reaction, the reacting solution is quenched with water and hydrochloric acid, the solvent layer is separated, and the product crystallized from solution.

The furan-3-carboxamide derivatives can also be made by using the foregoing process to obtain the basic furan-3-carboxamide structure (III), and then employing any well-known substitution reaction to provide a desired radical at any or all of the X, Y and Z positions as well as at the R position.

Of course, it must be fully understood that the one step reaction is equally applicable to those few known furan-3-carboxamide derivatives earlier noted, as well as to those novel compounds considered within the composition aspect of the invention.

The following examples illustrate the inventive method:

EXAMPLE 1

2-Methyl-4,5-diphenyl-3-carboxanilidofuran

A mixture of 0.05 mole (10.6g) benzoin, 0.05 mole (8.9g) acetoacetanilide 0.025 mole (3.3g.) aluminum chloride was refluxed in 50 ml. benzene with stirring for 30 minutes. The reaction was quenched with water (25 ml.) followed by 25 ml. 6N HCl. The benzene layer was separated, washed with water, then sodium hydroxide and finally water. The product was crystallized from methanol, m.p. 156°-159°, yield 28%.

EXAMPLE 2

2-Methyl-4,5-dipropyl-3-carboxanilidofuran

A mixture of 0.1 mole (14.4g.) butyroin, 0.1 mole (17.7g.) acetoacetanilide, 0.05 mole (6.7g.) aluminum chloride was refluxed and stirred in 50 ml. benzene for 30 minutes. The reaction mixture was treated as in Example 1. The product was crystallized from petroleum ether (60°-110°) m.p. 80°-82°, yield 28%.

EXAMPLE 3

2-Methyl-3-carboxanilidofuran

A mixture of 0.05 mole (3g.) glycolaldehyde, 0.05 mole (8.9g) acetoacetanilide, 0.025 mole (3.7g.) aluminum chloride was heated under reflux and stirred in 35 ml. benzene for 15 minutes. The reaction mixture which turned red was treated as in Example 1. A 45% yield of crude product m.p. 103°–108° was obtained.

EXAMPLE 4

2,4,5-Trimethyl 3-(o-phenylcarboxanilido) furan

A mixture of .05 mole (12.5 g.) o-phenylacetoacetanilide, 0.05 mole (4.4g.) acetoin, .025 mole (3.3 g.) AlCl$_3$ in 25 ml. benzene was stirred on a steam bath. Reaction did not appear to take place without warming. After 30 minutes of heating, water was added, followed by dilute hydrochloric acid. The benzene layer was separated, washed with more acid and water, followed by sodium hydroxide and water.

A 72% yield of desired product m.p. 106°–108° was obtained by precipitation with petroleum ether.

EXAMPLE 5

Preparation of 2,4,5-trimethyl-3-(o-methylcarboxanilido) furan

A mixture of 0.1 mole o-methylacetoacetanilide (19.1g) and 0.1 mole acetoin (8.8g.) was stirred in 75 ml. toluene on the steam bath. Aluminum chloride (0.05 mole, 6.7g.) was added in portions. After the initial reaction had subsided, stirring and heating was continued 30 minutes. Dilute hydrochloric acid was added and the two phase system allowed to crystallize. A yield of 76% 2,4,5-trimethyl-3-(o-methylcarboxanilido) furan was obtained m.p. 118.5° after filtration washing and drying.

EXAMPLE 6

2,4,5-Trimethyl-3-(o-methoxycarboxanilido) furan

A mixture of 0.1 mole o-methoxyacetoacetanilide (20.7g.) and 0.1 mole acetoin (8.8g.) was stirred and warmed in 75 ml. toluene while 0.05 mole aluminum chloride (6.7g.) was added in portions. After stirring and warming on steam bath thirty minutes, dilute hydrochloric acid was added and the product allowed to crystallize. A 70% yield of 2,4,5-trimethyl-3-(o-methoxycarboxanilido) furan m.p. 100.5° – 102° was obtained after filtering, washing and drying.

EXAMPLE 7

2,4,5-Trimethyl-3-carboxanilidofuran

To a stirred reaction mixture of acetoacetanilide (2 moles 354g.), dry acetoin (2 moles, 176g) (commercial grade dried by adding benzene, azeotroping off the water and then removing the benzene by distillation), and dry toluene (1500 ml.) was added aluminum chloride (1 mole 133 g.). The reaction mixture was stirred and cautiously heated to about 50° at which point the heating was discontinued and the temperature quickly rose exothermically to the boiling point. Some hydrogen chloride was evolved through the condenser thus lowering the boiling point of the toluene reaction mixture to about 95°. The reaction mixture was stirred and heated under reflux for one-half hour, allowed to cool to about 85°, water (300 ml) was cautiously added followed by 6 N hydrochloric acid (ca 200 ml). The hot reaction mixture was stirred for a few minutes, poured out into a beaker and allowed to cool to room temperature. The precipitated H719 was filtered, washed with dilute hydrochloric acid, with water and with toluene (ca 100 ml) and air dried. The yield of almost white H719 was 405 g., 88%, m.p. 138° – 139°, concentration of the toluene mother liquors gave a second crop 18 g., 4%, m.p. 134°–135°.

EXAMPLE 8

2,4-Dimethyl-3-carboxanilidofuran

A mixture of 0.1 mole acetoacetanilide (17.7g), and 0.1 mole acetol (CH$_3$COCH$_2$OH) (7.4g.) was stirred at room temperature in 50 ml. benzene. Aluminum chloride (0.1 mole, 13.3g.) was added. A vigorous reaction of short duration took place and after 15 min. stirring, water was added. The benzene layer was washed with hydrochloric acid, sodium hydroxide and finally water. A 37% yield of 2,4-dimethyl-3-carboxanilidofuran, m.p. 129°–130° was obtained.

EXAMPLE 9

2-Methyl-3-(o-methylcarboxanilido)furan

This was prepared as in example 3 from glycolaldehyde (CHOCH$_2$OH) and o-methylacetoacetanilide, m.p. 119°–121°, yield 55%.

EXAMPLE 10

2-Methyl-3-(o-methoxycarboxanilidofuran)

This was prepared from glycolaldehyde and o-methoxyacetoacetanilide in 65% yield as in Example 3; m.p. 61°–62°.

EXAMPLE 11

2-Methyl-5-t-butyl-3-carboxanilidofuran

A mixture of 0.1 mole (20.1g.) 2-methyl-3-carboxanilido furan and 0.1 mole (13.7 g.) t-butylbromide was stirred in 200 ml. carbon disulfide in an ice bath. 0.15 Mole (19.1g.) aluminum chloride was added portion wise. The mixture was then stirred at room temperature for 8 hours and let stand over night. It was poured onto ice and the precipitate filtered off and crystallized from xylene to give a 68% yield of 2-methyl-5-t-butyl-3-carboxanilidofuran m.p. 151°–152.5°.

EXAMPLE 12

2,4-Dimethyl-5-t-butyl-3-carboxanilidofuran

A mixture of 0.1 mole (21.5g.) 2,4-dimethyl-3-carboxanilidofuran and 0.1 mole (13.7g.) t-butyl bromide was stirred in 200 ml. carbon disulfide at room temperature and 0.15 mole (19.1g.) aluminum chloride added portion wise. The mixture was stirred 6 hours, let stand over night and then poured into ice. The carbon disulfide layer was separated, the aqueous layer was extracted with ether and added to it. Petroleum ether (60°–110°) was added to give 22 g. of white precipitate m.p. 127°–142°. The product was washed with a few ml. hot petroleum ether, to give a 30% yield of 2,4-dimethyl-5-t-butyl-3 carboxanilidofuran, m.p. 143°–147°.

EXAMPLE 13

2-Methyl-3-carboxanilido-4,5,6,7-tetrahydrobenzofuran

A mixture of 0.1 mole (11.4g) 2-hydroxycyclohexanone, 0.1 mole (17.7g) of acetoacetanilide, 0.05 mole (6.7g) aluminum chloride and 75 ml. of benzene was heated under reflux for 30 minutes. The reaction mixture was worked up as in example 1. The product was crystallized from benzene-petroleum ether (60°-110°), mp 119°-120°, yield 75%.

EXAMPLE 14

2-Phenyl-4,5-methyl-3-carboxanilidofuran

This was prepared as above from benzoylacetanilide ($C_6H_5CO\ CH_2\ CONH\ C_6H_5$), acetoin and aluminum chloride using toluene as solvent. The product melted at 167°-169° after crystallization from methanol, yield 34%.

EXAMPLE 15

2,4,5-Trimethyl-3-p-fluorocarboxanilidofuran

This was prepared as above from p-fluoroaceoacetanilide, acetoin and aluminum chloride using benzene as solvent. The product melted at 170.5°-171.5°, after crystallization from toluene, yield 80%.

EXAMPLE 16

2-Methyl-4-hydroxymethyl-3-carboxanilidofuran

This was prepared as above from acetoacetanilide, dihydroxyacetone ($HOCH_2COCH_2OH$) and aluminum chloride using benzene as solvent. The product melted at 120°-122° after crystallization from benzene petroleum ether (60°-110°), yield 7%.

EXAMPLE 17

2,4,5-Trimethyl-3-carboxanilido-N-benzoylfuran

To a solution of 2,4,5-trimethyl-3-carboxanilidofuran (15G) in chloroform (150ml) was added benzoyl chloride (15g) and triethylamine (15ml) and the solution was heated under reflux for 20 hours. The reaction mixture was cooled, washed with aqueous sodium hydroxide and with water and the solvent was removed. The residue which solidified was crystallized twice from isopropanol yielding 8g of white prisms melting at 120°-121°.

Yet another process can be used in making the compounds of the invention. However, this alternate process involves many steps and hence is decidedly inferior to the one step process described above. The multi-step process involves: (1) the reaction of an α-chloroketone or an α-hydroxyketone with ethyl acetoacetate to produce the furan-3-carboxylate; (2) the conversion of the product to the corresponding 3-furoic acid (3) the conversion of the acid into the corresponding 3-furoyl chloride by thionyl chloride, phosphorous pentachloride or other halogenating agents in inert solvents; (4) followed by conversion of the 3-furoyl chloride to a furan-3-carboxamide by treatment with a primary or secondary amine in an inert solvent.

The steps required to obtain the 3-furoic acid are well known. (See H. E. Winberg et al, J. Am. Chem. Soc. 82, 1428 (1960); F. G. Gonzalez et al, Anal. real. Soc. espan. Fis. Quim. 50B 407 (1954) C.A. 49 13206h (1955); O. Dann et al, Ber. 85, 457 (1952); J. C. Hanson et al, J. Chem, Soc. 1965 5984; and R. M. Acheson et al, J. Chem. Soc. 1952 1127-33.)

The following examples demonstrate the multistep method.

EXAMPLE 18

2-Methyl-3-N-allylcarboxamidofuran

Diethyl chloroacetal (1 mole, 152.6g.), and water (200 ml.), containing 6N hydrochloric acid (20 ml.) were heated under reflux (about 2 hours) until solution resulted. The acidic solution containing chloroacetaldehyde was neutralized with pyridine and added to a solution of ethyl acetoacetate (1 mole, 130g.) in pyridine (250 ml.) and stirred at room temperature for four hours. The oily layer containing ethyl 2-methyl-3-furoate was separated, washed with dilute hydrochloric acid and saponified by heating with a solution of sodium hydroxide (50g.) in water (300 ml.) and ethanol (300 ml.) for 4 hours. Acidification of the ethanolic solution precipitated 2-methyl-3-furoic acid which was filtered, washed and dried, m.p. 103°-106°.

2-Methyl-3-furoic acid (0.1 mole, 12.6g.) was suspended in benzene (50 ml.), thionyl chloride (0.11 mole, 13g.) was added and the reaction mixture was allowed to stand at room temperature for about twenty hours. The excess thionyl chloride and solvent were removed under reduced pressure. To the residue was added portion wise with cooling a solution of alkylamine (0.2 mole, 11.4g.) in about 50 ml. benzene and the reaction mixture let stand at room temperature for three hours. The benzene solution was washed with dilute hydrochloric acid and then diluted with petroleum ether (60°-110°) to precipitate 2-methyl-3-M-allylcarboxamidofuran, m.p. 46°-47°; yield 14 g. or 80%.

EXAMPLE 19

2,5-Dimethyl-3-carboxanilidofuran

To a stirred and refluxing solution of ethyl sodioacetoacetate (0.5 mole, 78g.) and sodium iodide (1g.) in dry acetone (250 ml.) was added chloroactone (0.54 mol. 50g.) over a period of ten minutes. After one hour the acetone was distilled from the reaction mixture and the residue was diluted with 400 ml. water. The preciptated oil was extracted with ether and the ether removed to yield the intermediate 3-carbethoxy-2,5-hexanedione (75g.). The intermediate (26.4g.) was cyclized by heating under reflux over 5 g. anhydrous oxalic acid for 1¼ hours. The crude ester was saponified by heating under reflux for 45 minutes with potassium hydroxide (26g.) in

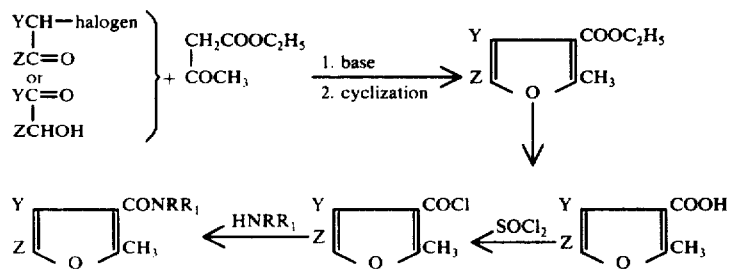

methanol (200 ml.). The methanol was removed, the residue dissolved in water and the solution acidified to yield 2,5-dimethyl-3-furoic acid (18g.), m.p. 130°-133°.

The acid (0.1 mole, 15 g.) was dissolved in chloroform, the solution treated with excess thionyl chloride and allowed to stand at room temperature overnight. The excess thionyl chloride and solvent were removed under reduced pressure, the residual acid chloride dissolved in benzene and the solution treated with aniline (0.2 mole, 18.6 g.) in benzene solution decolorized with Norite and diluted with petroleum ether to precipitate the title compound (17g.) m.p. 93°-94°.

EXAMPLE 20

2,4,5-Trimethyl-3-N,N-diethylcarboxamidofuran 1. 2,4,5-Trimethyl-3-furoic acid

A mixture of 3-hydroxy-2-butanone (90g.) ethyl acetoacetate (175g.), absolute ethanol (150 ml.) and anhydrous zinc chloride (100g.) was heated under reflux for 24 hours. The cooled solution was poured into water and extracted with benzene. The benzene extract was washed successively with 30% aqueous sodium bisulfite, 5% sodium hydroxide, dilute hydrochloric acid and finally with water. The solvent was removed and the residual ester saponified with aqueous-alcoholic alkali as in example 18 to yield 149 g. or 96% yield of the 2,4,5-trimethyl-3-furoic acid.

2. 2,4,5-Trimethyl-3-furoic acid

To a stirred and refluxing solution of ethyl sodioacetoacetate (153 g.), sodium iodide (2 g.) and dry acetone (500 ml.) was added 3-chloro-2-butanone (1.1 mol., 117 g.) and the refluxing and stirring continued for 1½ hours. The precipitated sodium chloride was filtered off from the reaction mixture and the acetone was removed from the filtrate. To the residue, water was added and the oily intermediate extracted with benzene. The benzene solution was treated with p-toluenesulfonic acid (0.5g.) and heated under reflux collecting the water of cyclization-dehydration in a Dean-Stark trap. After the reaction was completed (2-4 hours) the benzene was removed and the residual ester was saponified as in example 18 to give 117 g. (yield 76%) of 2,4,5-trimethylfuroic acid.

The acid (0.1 mole, 15.4g.) was suspended in benzene, the solution treated with thionyl chloride (13g.) and allowed to stand at room temperature overnight. The excess thionyl chloride and solvent were removed under reduced pressure, the residue treated with diethylamine (0.2 mole, 14.8g.) in benzene (50 ml.) with cooling and the reaction mixture was allowed to stand at room temperature for three hours. The benzene solution was washed with 5% aqueous sodium hydroxide, with dilute hydrochloric acid and with water. The solvent was removed to yield the oily title compound (10g., 48%).

EXAMPLE 21

2-n-Heptadecyl-4,5-dimethyl-3-carboxyfuran was prepared from ethyl stearoylacetate and 3-hydroxy-2-butanone as in example 20. This was converted to the anilide via the acid chloride in the usual manner. The yield was 30%.

Other examples of Furan-3-Carboxanilides

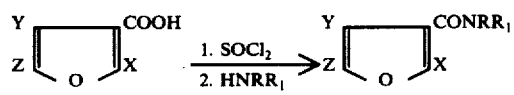

| Ex. No. | Name of the 3-substituent | R | R₁ | X | Y | Z | m.p. |
|---|---|---|---|---|---|---|---|
| 22. | N-Isopropyl-carboxamido | H | —CH(CH₃)₂ | CH₃ | H | H | 84–86 |
| 23. | N-n-Butyl-carboxamido | H | —C₄H₉ | CH₃ | H | H | oil |
| 24. | N-Cyclohexylcarboxamido | H | (cyclohexyl) | CH₃ | H | H | 99–100 |
| 25. | m-Methyl-carboxanilido | H | (m-methylphenyl) | CH₃ | H | H | 91–91.5 |
| 26. | p-Methyl-carboxanilido | H | (p-methylphenyl) | CH₃ | H | H | 80–82° |
| 27. | m-Methoxy-carboxanilido | H | (m-methoxyphenyl) | CH₃ | H | H | oil |
| 28. | p-Methoxy-carboxanilido | H | (p-methoxyphenyl) | CH₃ | H | H | 108–109° |

-continued

Other examples of Furan-3-Carboxanilides

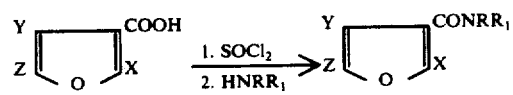

| Ex. No. | Name of the 3-substituent | R | $R_1$ | X | Y | Z | m.p. |
|---|---|---|---|---|---|---|---|
| 29. | p-Nitro-carboxanilido | H | $p$-$NO_2$-$C_6H_4$- | $CH_3$ | H | H | 179–180 |
| 30. | o-Phenylcarboxanilido | H | $o$-$Ph$-$C_6H_4$- | $CH_3$ | H | H | oil |
| 31. | N,2-Thiazolylcarboxamido | H | 2-thiazolyl | $CH_3$ | H | H | 162–163.5 |
| 32. | 2,6-Dimethylcarboxanilido | H | 2,6-($CH_3$)$_2$-$C_6H_3$- | $CH_3$ | H | H | 146–148° |
| 33. | 2,4,6-trimethylcarboxanilido | H | 2,4,6-($CH_3$)$_3$-$C_6H_2$- | $CH_3$ | H | H | 155–156 |
| 34. |  | H | $CONHCH_2CH_2$-furyl-$CH_3$ | $CH_3$ | H | H | 174–175 |
| 35. | N-Allyl-carboxamido | H | $CH_2=CHCH_2-$ | $CH_3$ | $CH_3$ | $CH_3$ | 70–72° |
| 36. | N-Isopropylcarboxamido | H | $-CH(CH_3)_2$ | $CH_3$ | $CH_3$ | $CH_3$ | 118–120° |
| 37. | N-n-Butylcarboxamido | H | n-$C_4H_9$ | $CH_3$ | $CH_3$ | $CH_3$ | 77–79 |
| 38. | N-n-Decylcarboxamido | H | n-$C_{10}H_{21}$ | $CH_3$ | $CH_3$ | $CH_3$ | oil |
| 39. | N-Benzylcarboxamido | H | $C_6H_5$-$CH_2-$ | $CH_3$ | $CH_3$ | $CH_3$ | 104–106 |
| 40. | N-Cyclohexylcarboxamido | H | cyclohexyl | $CH_3$ | $CH_3$ | $CH_3$ | 158–160 |
| 41. | Carboxmorpholido | $R_1$ & $R_2$ together | morpholino | $CH_3$ | $CH_3$ | $CH_3$ | 59–61° |
| 42. | N-2-Pyridylcarboxamido | H | 2-pyridyl | $CH_3$ | $CH_3$ | $CH_3$ | 116–118° |
| 43. | N-Methylcarboxanilido | $CH_3$ | $C_6H_5$ | $CH_3$ | $CH_3$ | $CH_3$ | oil |
| 44. | m-Methylcarboxanilido | H | $m$-$CH_3$-$C_6H_4$-($C_6H_5$) | $CH_3$ | $CH_3$ | $CH_3$ | 131–132° |

-continued

Other examples of Furan-3-Carboxanilides

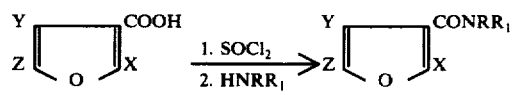

| Ex. No. | Name of the 3-substituent | R | R₁ | X | Y | Z | m.p. |
|---|---|---|---|---|---|---|---|
| 45. | m-Methoxycarboxanilido | H | 3-CH₃O-C₆H₄ | CH₃ | CH₃ | CH₃ | 95–97° |
| 46. | p-Methoxycarboxanilido | H | 4-CH₃O-C₆H₄ | CH₃ | CH₃ | CH₃ | 162.163.5° |
| 47. | p-Chlorocarboxanilido | H | 4-Cl-C₆H₄ | CH₃ | CH₃ | CH₃ | 175–177 |
| 48. | α-Napthylcarboxamido | H | α-naphthyl | CH₃ | CH₃ | CH₃ | 145–146 |
| 49. | β-Naphthylcarboxamido | H | β-naphthyl | CH₃ | CH₃ | CH₃ | 142–144 |
| 50. | 2,6-Dimethylcarboxanilido | H | 2,6-(CH₃)₂-C₆H₃ | CH₃ | CH₃ | CH₃ | 143.5–145° |
| 51. | 2-Methyl-6-chlorocarboxanilido | H | 2-CH₃-6-Cl-C₆H₃ | CH₃ | CH₃ | CH₃ | 147–148.5 |
| 52. | 2,4,6-Trimethylcarboxanilido | H | 2,4,6-(CH₃)₃-C₆H₂ | CH₃ | CH₃ | CH₃ | 144–146° |
| 53. | Carboxanilido | H | C₆H₅ | C₃H₇ | CH₃ | CH₃ | 127–128.5° |
| 54. | Carboxanilido | H | C₆H₅ | C₆H₅ | CH₃ | CH₃ | 168–169° |
| 55. | N-Furfurylcarboxamido | H | furfuryl (2-furyl-CH₂–) | CH₃ | CH₃ | CH₃ | 96–97° |

EXAMPLE 56

2,4,5-trimethyl-3-carboxanilido-N-trichloromethylsulfenylfuran

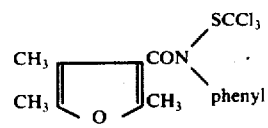

2,4,5-trimethyl-3-carboxanilidofuran was heated in a benzene solution with sodium hydride until the evolution of hydrogen ceased; excess trichloromethylsulfenyl chloride (Cl₃CSCl) was added and heat was again applied to produce the product, m.p. 92°–94°.

Having thus described our invention, what we claim and desire to protect by Letters Patent is:

1. A compound having the structural formula

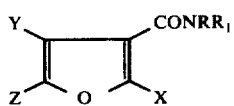

wherein R is hydrogen, alkyl of 1 to 2 carbon atoms, benzoyl, or trichloromethylsulfenyl; $R_1$ is phenyl, alkylphenyl, alkoxyphenyl, halophenyl, nitrophenyl, benzyl, biphenylyl, alkyl having from 1 to 10 carbon atoms, allyl, cyclohexyl, naphthyl, pyridyl, thiazolyl, ethylene bis-, or furfuryl; or R and $R_1$ taken together are oxydiethylene; Y and Z are independently selected from the group consisting of hydrogen, halo, amino, alkyl having 1 to 17 carbon atoms, hydroxyalkyl of 1 to 17 carbon atoms, chloroalkyl of 1 to 17 carbon atoms, nitroalkyl of 1 to 17 carbon atoms, allyl, phenyl, alkylphenyl, alkoxyphenyl, halophenyl, or Y and Z together are, alkylene; and X is either alkyl having from 1 to 17 carbon atoms or phenyl; provided that if

| if | (R | is H | ) | |
|---|---|---|---|---|
| | ($R_1$ | is phenyl | ) | |
| | (X | is $CH_3$ | ) | |
| | (Z | is H | ) | , then Y is not H or $CH_3$. | then Y is not H or $CH_3$.

2. The compound of claim 1, wherein R is hydrogen, alkyl having 1 to 2 carbon atoms, benzoyl, or trichloromethylsulfenyl; $R_1$ is phenyl, a methyl-substituted phenyl, methoxyphenyl fluorophenyl, a chloro-substituted phenyl, nitrophenyl, benzyl, biphenylyl, alkyl having 1 to 10 carbon atoms, allyl, cyclohexyl, naphthyl, pyridyl, thiazolyl, ethylene bis-, or furfuryl; or R and $R_1$ taken together are oxydiethylene; Y is hydrogen, alkyl having 1 to 3 carbon atoms, or hydroxymethyl; Z is hydrogen, alkyl having 1 to 4 carbon atoms, or phenyl; or Y and Z taken together are tetramethylene; and X is either alkyl having 1 to 17 carbon atoms or phenyl; provided that if

| if | (R | is H | ) | |
|---|---|---|---|---|
| | ($R_1$ | is phenyl | ) | |
| | (X | is $CH_3$ | ) | |
| | (Z | is H | ) | , then Y is not H or $CH_3$. | then Y is not H or $CH_3$.

3. The compound of claim 1, wherein $R_1$ is cyclohexyl.

4. The compound of claim 3, wherein R is hydrogen.

5. The compound of claim 1, wherein $R_1$ is phenyl.

6. The compound of claim 5, wherein R is hydrogen.

7. The compound of claim 1, wherein R is hydrogen, $R_1$ is cyclohexyl, X is methyl, and Y and Z are hydrogen.

8. The compound of claim 1, wherein R is hydrogen, $R_1$ is cyclohexyl, and each of X, Y and Z is methyl.

9. The compound of claim 1, wherein R is hydrogen, $R_1$ is o-methylphenyl, X is methyl, and Y and Z are hydrogen.

10. The compound of claim 1, wherein R is hydrogen, $R_1$ is o-methylphenyl, and each of X, Y and Z is methyl.

11. The compound of claim 1, wherein R is hydrogen, $R_1$ is m-methylphenyl, X is methyl, and Y and Z are hydrogen.

12. The compound of claim 1, wherein R is hydrogen, $R_1$ is m-methoxyphenyl, X is methyl, and Y and Z are hydrogen.

13. The compound of claim 1, wherein R is hydrogen, $R_1$ is p-methoxyphenyl, and each of X, Y and Z is methyl.

14. 2,4,5-trimethylfuran-3-carboxanilide.

15. 2,5-dimethylfuran-3-carboxanilide.

16. A method of making a compound of the formula:

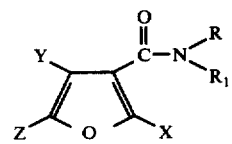

wherein X, Y and Z are independently selected from the group consisting of hydrogen, alkyl containing 1 to 17 carbon atoms, lower hydroxyalkyl, allyl, phenyl, lower alkoxyphenyl, lower alkylphenyl, nitrophenyl and halophenyl, or Y and Z together are 1,4-butylene; R is selected from the group consisting of hydrogen, alkyl containing 1 to 10 carbon atoms, benzoyl and trichloromethyl sulfenyl; and $R_1$ is selected from the group consisting of phenyl, lower alkylphenyl, lower alkoxyphenyl, halophenyl, nitrophenyl, benzyl, biphenylyl, alkyl containing 1 to 10 carbon atoms, allyl, cyclohexyl, naphthyl, pyridyl, thiazolyl, ethylene bis-, and furfuryl, or R and $R_1$ together with the nitrogen is morpholino, said method comprising reacting an alphahydroxyketone or aldehyde of the formula

with an acetamide of the formula

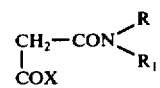

where X, Y, Z, R and $R_1$ have the meanings set forth above in this claim, in an inert, non-hydroxylic solvent and in the presence of an active Friedel-Crafts reagent selected from the group consisting of $AlCl_3$, $AlBr_3$ and $SnCl_4$.

17. The method of claim 16 wherein about equimolar amounts of said alpha-hydroxyketone or aldehyde and acetamide are used, and about 0.5 mole of said Friedel- Crafts reagent is present for each mole of alpha-hydroxyketone or aldehyde or acetamide.

18. The method of claim 16 wherein about equimolar amounts of said alpha-hydroxyketone or aldehyde and acetamide are used and about 0.01 to 0.5 mole of said Friedel-Crafts reagent is present for each mole of alpha-hydroxyketone or aldehyde or acetamide, together with means for removing water formed by the reaction.

19. The method of producing 2,4,5-trimethylfuran-3-carboxanilide which comprises reacting acetoin with acetoacetanilide in an inert, non-hydroxylic solvent and in the presence of an active Friedel-Crafts reagent selected from the group consisting of $AlCl_3$, $AlBr_3$ and $SnCl_4$.

20. The method of producing 2,4,5-trimethylfuran-3-methylcarboxanilide which comprises reacting acetoin with methylacetoacetanilide in an inert, non-hydroxylic solvent and in the presence of an active Friedel-Crafts reagent selected from the group consisting of $AlCl_3$, $AlBr_3$ and $SnCl_4$.

21. The method of producing 2,4,5-trimethylfuran-3-methoxycarboxanilide which comprises reacting acetoin with methoxyacetoacetanilide in an inert, non-hydroxylic solvent and in the presence of an active Friedel-Crafts reagent selected from the group consisting of $AlCl_3$, $AlBr_3$ and $SnCl_4$.

* * * * *